US010519605B2

(12) United States Patent
Jung et al.

(10) Patent No.: US 10,519,605 B2
(45) Date of Patent: Dec. 31, 2019

(54) METHOD OF MARKING CELLULOSIC PRODUCTS

(71) Applicant: APDN (B.V.I.) Inc., Tortola (VG)

(72) Inventors: Lawrence Jung, Dix Hills, NY (US); Michael E. Hogan, Stony Brook, NY (US); Ming Hwa Benjamin Liang, East Setauket, NY (US)

(73) Assignee: APDN (B.V.I.), Inc., Tortola (VG)

( * ) Notice: Subject to any disclaimer, the term of this patent is extended or adjusted under 35 U.S.C. 154(b) by 286 days.

(21) Appl. No.: 15/466,016

(22) Filed: Mar. 22, 2017

(65) Prior Publication Data

US 2017/0292206 A1 Oct. 12, 2017

Related U.S. Application Data

(60) Provisional application No. 62/320,946, filed on Apr. 11, 2016.

(51) Int. Cl.
| | | |
|---|---|---|
| *D21H 21/44* | (2006.01) | |
| *C12Q 1/6876* | (2018.01) | |
| *D01F 1/06* | (2006.01) | |
| *D01F 2/00* | (2006.01) | |

(52) U.S. Cl.
CPC ......... *D21H 21/44* (2013.01); *C12Q 1/6876* (2013.01); *D01F 1/06* (2013.01); *D01F 2/00* (2013.01)

(58) Field of Classification Search
None
See application file for complete search history.

(56) References Cited

U.S. PATENT DOCUMENTS

| | | | |
|---|---|---|---|
| 4,183,989 A | 1/1980 | Tooth | |
| 4,278,557 A | 7/1981 | Elwell, Jr. | |
| 4,454,171 A | 6/1984 | Diggle, Jr. et al. | |
| 4,548,955 A | 10/1985 | Okahata et al. | |
| 4,683,195 A | 7/1987 | Mullis et al. | |
| 4,683,202 A | 7/1987 | Mullis | |
| 4,739,044 A | 4/1988 | Stabinsky | |
| 4,757,141 A | 7/1988 | Fung et al. | |
| 4,861,620 A | 8/1989 | Azuma et al. | |
| 4,965,188 A | 10/1990 | Mullis et al. | |
| 5,047,519 A | 9/1991 | Hobbs, Jr. et al. | |
| 5,075,216 A | 12/1991 | Innis et al. | |
| 5,089,691 A | 2/1992 | Morisaki et al. | |
| 5,132,242 A | 7/1992 | Cheung | |
| 5,139,812 A | 8/1992 | Lebacq | |
| 5,151,507 A | 9/1992 | Hobbs, Jr. et al. | |
| 5,156,765 A | 10/1992 | Smrt et al. | |
| 5,176,203 A | 1/1993 | Larzul | |
| 5,270,183 A | 12/1993 | Corbett et al. | |
| 5,415,839 A | 5/1995 | Zaun et al. | |
| 5,429,952 A | 7/1995 | Garner et al. | |
| 5,451,505 A | 9/1995 | Dollinger | |
| 5,498,283 A | 3/1996 | Botros et al. | |
| 5,508,197 A | 4/1996 | Hansen et al. | |
| 5,595,871 A | 1/1997 | DelVecchio et al. | |
| 5,599,578 A | 2/1997 | Butland | |
| 5,602,381 A | 2/1997 | Hoshino et al. | |
| 5,639,603 A | 6/1997 | Dower et al. | |
| 5,643,728 A | 7/1997 | Slater et al. | |
| 5,725,821 A * | 3/1998 | Gannon | D01F 2/00 264/203 |
| 5,736,314 A | 4/1998 | Hayes et al. | |
| 5,763,176 A | 6/1998 | Slater et al. | |
| 5,776,713 A | 7/1998 | Garner et al. | |
| 5,849,208 A | 12/1998 | Hayes et al. | |
| 5,866,336 A | 2/1999 | Nazarenko et al. | |
| 5,912,257 A | 6/1999 | Prasad et al. | |
| 5,942,444 A | 8/1999 | Rittenburg et al. | |
| 5,956,172 A | 9/1999 | Downing | |
| 5,977,436 A | 11/1999 | Thomas et al. | |
| 5,989,823 A | 11/1999 | Jayasena et al. | |
| 6,013,789 A | 1/2000 | Rampal | |
| 6,030,657 A | 2/2000 | Butland et al. | |
| 6,033,880 A | 3/2000 | Haff et al. | |
| 6,057,370 A | 5/2000 | Weiland et al. | |
| 6,127,120 A | 10/2000 | Graham et al. | |
| 6,132,996 A | 10/2000 | Hunicke-Smith | |
| 6,140,075 A | 10/2000 | Russell et al. | |
| 6,169,174 B1 | 1/2001 | Hasegawa et al. | |

(Continued)

FOREIGN PATENT DOCUMENTS

| | | |
|---|---|---|
| EP | 0623658 A2 | 11/1994 |
| EP | 0477220 B1 | 9/1996 |

(Continued)

OTHER PUBLICATIONS

Kim, Jeong Ah et al., "Fabrication and Characterization of a PDMS-Glass Hybrid Continuous-Flow PCR Chip", Biochemical Engineering Journal, 29, 91-97 (2006).
Curcio, Mario et al., "Continuous Segmented-Flow Poymerase Chain Reaction for High-Throughput Miniaturized DNA Amplification" Analytical Chemistry, vol. 75, No. 1, 1-7 ( Jan. 1, 2003).
Kopp, Martin U. et al, "Chemical Amplification: Continuous-Flow PCR on a Chip", Science, vol. 280, 1046-1048 (1998).
Skirtach, Andre, G. et al, "The Role of Metal Nanoparticles in Remote Release of Encapsulated Materials", Nano Letters, vol. 5, No. 7, 1371-1377 (2005).
Fixe, F. et al., Thin Film Micro Arrays with Immobilized DNA for Hybridization Analysis, Mat. Res. Soc. Symp. Proc. vol. 723, Materials Research Society, O2.3.1-O2.3.6 (2002).

(Continued)

*Primary Examiner* — Samuel C Woolwine
(74) *Attorney, Agent, or Firm* — Allen, Dyer, Doppelt & Gilchrist, P.A.

(57) ABSTRACT

Methods for marking cellulosic products, including cellulosic fibers such as lyocell and cellulosic films, including methods for marking such products with a detectable nucleic acid marker to identify and validate the origin or authenticity of the products or items manufactured using such products. Detectably-marked cellulosic products marked with nucleic acid markers for authentication, validation and tracking are also provided.

11 Claims, 3 Drawing Sheets

(56) References Cited

U.S. PATENT DOCUMENTS

| | | |
|---|---|---|
| 6,261,809 B1 | 7/2001 | Bertling et al. |
| 6,287,768 B1 | 9/2001 | Chenchik et al. |
| 6,312,911 B1 | 11/2001 | Bancroft et al. |
| 6,326,489 B1 | 12/2001 | Church et al. |
| 6,342,359 B1 | 1/2002 | Lee et al. |
| 6,361,944 B1 | 3/2002 | Mirkin et al. |
| 6,379,897 B1 | 4/2002 | Weidenhammer et al. |
| 6,399,397 B1 | 6/2002 | Zarling et al. |
| 6,537,747 B1 | 3/2003 | Mills, Jr. et al. |
| 6,537,752 B1 | 3/2003 | Astle |
| 6,576,422 B1 | 6/2003 | Weinstein et al. |
| 6,608,228 B1 | 8/2003 | Cumpston et al. |
| 6,613,560 B1 | 9/2003 | Tso et al. |
| 6,632,653 B1 | 10/2003 | Astle |
| 6,686,149 B1 | 2/2004 | Sanchis et al. |
| 6,703,228 B1 | 3/2004 | Landers et al. |
| 6,709,692 B2 | 3/2004 | Sudor |
| 6,743,640 B2 | 6/2004 | Whitten et al. |
| 6,995,256 B1 | 2/2006 | Li et al. |
| 7,014,113 B1 | 3/2006 | Powell et al. |
| 7,015,030 B1 | 3/2006 | Fouillet et al. |
| 7,031,927 B1 | 4/2006 | Beck et al. |
| 7,060,874 B2 | 6/2006 | Wilkins |
| 7,112,616 B2 | 9/2006 | Takizawa et al. |
| 7,115,301 B2 | 10/2006 | Sheu et al. |
| 7,133,726 B1 | 11/2006 | Atwood et al. |
| 7,160,996 B1 | 1/2007 | Cook |
| 7,223,906 B2 | 5/2007 | Davis |
| 7,250,195 B1 | 7/2007 | Storey et al. |
| 7,709,250 B2 | 5/2010 | Corbett et al. |
| 7,732,492 B2 | 6/2010 | Makino et al. |
| 8,278,807 B2 | 10/2012 | Agneray et al. |
| 8,597,549 B2 | 12/2013 | Cumpston et al. |
| 9,266,370 B2 | 2/2016 | Jung et al. |
| 9,297,032 B2 | 3/2016 | Jung et al. |
| 2001/0039018 A1 | 11/2001 | Matson et al. |
| 2002/0048822 A1 | 4/2002 | Rittenburg et al. |
| 2002/0051969 A1 | 5/2002 | Goto et al. |
| 2002/0056147 A1 | 5/2002 | Dau et al. |
| 2002/0064639 A1 | 5/2002 | Rearick et al. |
| 2002/0080994 A1 | 6/2002 | Lofgren et al. |
| 2002/0119485 A1 | 8/2002 | Morgan |
| 2002/0128234 A1 | 9/2002 | Hubbell et al. |
| 2002/0129251 A1 | 9/2002 | Itakura et al. |
| 2002/0137893 A1 | 9/2002 | Burton et al. |
| 2002/0155490 A1 | 10/2002 | Skinner et al. |
| 2002/0160360 A1 | 10/2002 | Chenchik et al. |
| 2002/0167161 A1 | 11/2002 | Butland |
| 2002/0185634 A1 | 12/2002 | Marder et al. |
| 2002/0187263 A1 | 12/2002 | Sheu et al. |
| 2003/0000225 A1 | 1/2003 | Nagai et al. |
| 2003/0017551 A1 | 1/2003 | Parthasarathy et al. |
| 2003/0035917 A1 | 2/2003 | Hyman |
| 2003/0064507 A1 | 4/2003 | Gallagher et al. |
| 2003/0096273 A1 | 5/2003 | Gagna |
| 2003/0142704 A1 | 7/2003 | Lawandy |
| 2003/0142713 A1 | 7/2003 | Lawandy |
| 2003/0162296 A1 | 8/2003 | Lawandy |
| 2003/0177095 A1 | 9/2003 | Zorab et al. |
| 2003/0203387 A1 | 10/2003 | Pelletier |
| 2003/0207331 A1 | 11/2003 | Wilson, Jr. et al. |
| 2004/0063117 A1 | 4/2004 | Rancien et al. |
| 2004/0071718 A1 | 4/2004 | Tsai |
| 2004/0115796 A1 | 6/2004 | Burns |
| 2004/0166520 A1 | 8/2004 | Connolly |
| 2004/0219287 A1 | 11/2004 | Regan et al. |
| 2005/0008762 A1 | 1/2005 | Sheu et al. |
| 2005/0031120 A1 | 2/2005 | Samid |
| 2005/0045063 A1 | 3/2005 | Niggemann et al. |
| 2005/0053968 A1 | 3/2005 | Bharadwaj et al. |
| 2005/0059029 A1 | 3/2005 | Mariella, Jr. et al. |
| 2005/0059059 A1 | 3/2005 | Liang |
| 2005/0112610 A1 | 5/2005 | Lee et al. |
| 2005/0142565 A1 | 6/2005 | Samper et al. |
| 2005/0214532 A1 | 9/2005 | Kosak et al. |
| 2005/0260609 A1 | 11/2005 | Lapidus |
| 2006/0017957 A1 | 1/2006 | Degott et al. |
| 2006/0017959 A1 | 1/2006 | Downer et al. |
| 2006/0117465 A1 | 6/2006 | Willows et al. |
| 2006/0121181 A1 | 6/2006 | Sleat et al. |
| 2006/0199196 A1 | 9/2006 | O'Banion et al. |
| 2006/0286569 A1 | 12/2006 | Bar-Or et al. |
| 2007/0012784 A1 | 1/2007 | Mercolino |
| 2007/0026239 A1 | 2/2007 | Sigrist et al. |
| 2007/0048761 A1 | 3/2007 | Reep et al. |
| 2007/0072197 A1 | 3/2007 | Rayms-Keller et al. |
| 2007/0117119 A1 | 5/2007 | Akita et al. |
| 2007/0121937 A1 | 5/2007 | Kochevar et al. |
| 2007/0254292 A1 | 11/2007 | Fukasawa et al. |
| 2008/0038813 A1 | 2/2008 | Chen |
| 2008/0081357 A1 | 4/2008 | Kwon et al. |
| 2008/0149713 A1 | 6/2008 | Brundage |
| 2008/0153135 A1 | 6/2008 | Liu |
| 2008/0216255 A1 | 9/2008 | Poovey et al. |
| 2008/0290649 A1 | 11/2008 | Klein et al. |
| 2008/0293052 A1 | 11/2008 | Liang et al. |
| 2008/0299559 A1 | 12/2008 | Kwok et al. |
| 2008/0299667 A1 | 12/2008 | Kwok et al. |
| 2008/0312427 A1 | 12/2008 | Kwok et al. |
| 2009/0042191 A1 | 2/2009 | Hayward et al. |
| 2009/0057147 A1 | 3/2009 | Kayyem |
| 2009/0069199 A1 | 3/2009 | Brandenburg |
| 2009/0075261 A1 | 3/2009 | Hayward et al. |
| 2009/0136163 A1 | 5/2009 | Kerr et al. |
| 2009/0220789 A1 | 9/2009 | DeSimone et al. |
| 2009/0222912 A1 | 9/2009 | Boschin |
| 2009/0253127 A1 | 10/2009 | Gaudreau et al. |
| 2009/0286250 A1 | 11/2009 | Hayward et al. |
| 2009/0311555 A1 | 12/2009 | Badyal et al. |
| 2009/0313740 A1 | 12/2009 | Santos et al. |
| 2009/0325234 A1 | 12/2009 | Gregg et al. |
| 2010/0050344 A1 | 3/2010 | Peltz et al. |
| 2010/0065463 A1 | 3/2010 | Taylor |
| 2010/0075407 A1 | 3/2010 | Duffy et al. |
| 2010/0075858 A1 | 3/2010 | Davis et al. |
| 2010/0099080 A1 | 4/2010 | Church et al. |
| 2010/0149531 A1 | 6/2010 | Tang |
| 2010/0240101 A1 | 9/2010 | Lieberman et al. |
| 2010/0250616 A1 | 9/2010 | Kim |
| 2010/0258743 A1 | 10/2010 | Bortolin |
| 2010/0267091 A1 | 10/2010 | Murray et al. |
| 2010/0279282 A1 | 11/2010 | Liang et al. |
| 2010/0285447 A1 | 11/2010 | Walsh et al. |
| 2010/0285490 A1 | 11/2010 | Dees et al. |
| 2010/0285985 A1 | 11/2010 | Liang et al. |
| 2010/0307120 A1 | 12/2010 | Stover |
| 2011/0054938 A1 | 3/2011 | Hood et al. |
| 2011/0165569 A1 | 7/2011 | Macula |
| 2011/0229881 A1 | 9/2011 | Oshima et al. |
| 2011/0250594 A1 | 10/2011 | Liang et al. |
| 2011/0263688 A1 | 10/2011 | Barany et al. |
| 2012/0115154 A1 | 5/2012 | Hampikian |
| 2012/0264742 A1 | 10/2012 | Furuishi et al. |
| 2013/0040150 A1 | 2/2013 | Trexler et al. |
| 2013/0040381 A1 | 2/2013 | Gregg et al. |
| 2013/0046994 A1 | 2/2013 | Shaw |
| 2013/0048731 A1 | 2/2013 | Flickner et al. |
| 2013/0109596 A1 | 5/2013 | Peterson et al. |
| 2013/0149706 A1 | 6/2013 | Kwok et al. |
| 2013/0234043 A1 | 9/2013 | Hussain et al. |
| 2013/0274129 A1 | 10/2013 | Katzen et al. |
| 2014/0099643 A1 | 4/2014 | Jung et al. |
| 2014/0106357 A1 | 4/2014 | Berrada et al. |
| 2014/0224673 A1 | 8/2014 | Alocilja |
| 2014/0256881 A1 | 9/2014 | Berrada et al. |
| 2014/0272097 A1 | 9/2014 | Jung et al. |
| 2014/0295423 A1 | 10/2014 | Liang et al. |
| 2015/0018538 A1 | 1/2015 | Berrada et al. |
| 2015/0030545 A1 | 1/2015 | Grass et al. |
| 2015/0083797 A1 | 3/2015 | Tran et al. |
| 2015/0104800 A1 | 4/2015 | Lee et al. |
| 2015/0107475 A1 | 4/2015 | Jung et al. |
| 2015/0125949 A1 | 5/2015 | Liss |
| 2015/0133319 A1 | 5/2015 | Fu et al. |

(56) References Cited

U.S. PATENT DOCUMENTS

| | | |
|---|---|---|
| 2015/0141264 A1 | 5/2015 | Jung et al. |
| 2015/0191799 A1 | 7/2015 | Liang et al. |
| 2015/0232952 A1 | 8/2015 | Sun et al. |
| 2015/0266332 A1 | 9/2015 | Szczepanik et al. |
| 2015/0275271 A1 | 10/2015 | Berrada et al. |
| 2015/0302713 A1 | 10/2015 | Berrada et al. |
| 2015/0304109 A1 | 10/2015 | Tran et al. |
| 2015/0329856 A1 | 11/2015 | Liang et al. |
| 2016/0076088 A1 | 3/2016 | Tran et al. |
| 2016/0102215 A1 | 4/2016 | Hayward et al. |
| 2016/0168781 A1 | 6/2016 | Tran et al. |
| 2016/0246892 A1 | 8/2016 | Murrah et al. |
| 2016/0264687 A1 | 9/2016 | Tran |
| 2016/0326511 A1 | 11/2016 | Berrada et al. |
| 2016/0362723 A1 | 12/2016 | Jung et al. |
| 2017/0021611 A1 | 1/2017 | Jung et al. |

FOREIGN PATENT DOCUMENTS

| | | |
|---|---|---|
| EP | 0840350 A2 | 5/1998 |
| EP | 1063286 A1 | 12/2000 |
| EP | 1231470 A1 | 8/2002 |
| EP | 1237327 A2 | 9/2002 |
| EP | 1403333 A1 | 3/2004 |
| EP | 1847316 A1 | 10/2007 |
| EP | 2428925 A1 | 3/2012 |
| EP | 2444136 A1 | 4/2012 |
| EP | 2444546 A1 | 4/2012 |
| GB | 2319337 A | 5/1998 |
| GB | 2434570 A | 8/2007 |
| JP | 63-503242 | 11/1988 |
| JP | 2009517250 A | 4/2009 |
| RU | 2084535 C1 | 7/1997 |
| RU | 2170084 C1 | 7/2001 |
| WO | 87/06383 A1 | 10/1987 |
| WO | 90/14441 A1 | 11/1990 |
| WO | 92/04469 A2 | 3/1992 |
| WO | 95/02702 A1 | 1/1995 |
| WO | 95/06249 A1 | 3/1995 |
| WO | 97/04392 A1 | 2/1997 |
| WO | 97/45539 A1 | 12/1997 |
| WO | 98/06084 A1 | 2/1998 |
| WO | 98/16313 A1 | 4/1998 |
| WO | 99/45514 A1 | 9/1999 |
| WO | 99/59011 A1 | 11/1999 |
| WO | 00/55609 A2 | 9/2000 |
| WO | 00/61799 A2 | 10/2000 |
| WO | 01/25002 A1 | 4/2001 |
| WO | 01/36676 A2 | 5/2001 |
| WO | 01/99063 A1 | 12/2001 |
| WO | 02/057548 A1 | 7/2002 |
| WO | 02/066678 A2 | 8/2002 |
| WO | 02/084617 A1 | 10/2002 |
| WO | 03/016558 A1 | 2/2003 |
| WO | 03/030129 A2 | 4/2003 |
| WO | 03/038000 A1 | 5/2003 |
| WO | 03/080931 A1 | 10/2003 |
| WO | 2004/025562 A1 | 3/2004 |
| WO | 2004/086323 A1 | 10/2004 |
| WO | 2005/075683 A1 | 8/2005 |
| WO | 2005/103226 A2 | 11/2005 |
| WO | 2006/109014 A1 | 10/2006 |
| WO | 2007/078833 A2 | 7/2007 |
| WO | 2008/007060 A1 | 1/2008 |
| WO | 2008045288 A2 | 4/2008 |
| WO | 2008/154931 A1 | 12/2008 |
| WO | 2012/076021 A1 | 6/2012 |
| WO | 2013/052924 A1 | 4/2013 |
| WO | 2013/154943 A1 | 10/2013 |
| WO | 2013/170009 A1 | 11/2013 |
| WO | 2014/062754 A1 | 4/2014 |

OTHER PUBLICATIONS

Hayward, Jim et al., "A Scaled, Integrative Implementation for DNA Marking of Integrated Circuits", Applied DNA Sciences, 1-25 (2013).

Ovsianikov, Aleksandr et al., "Two-Photon Polymerization Technique for Microfabrication of CAD-Designed 3D Scaffolds from Commercially Available Photosensitive Materials", Journal of Tissue Engineering and Regenerative Medicine, 1:443-449 (2007).

Khandjian, E.W., "Optimized Hybridization of DNA Blotted and Fixed to Nitrocellulose and Nylon Membranes" Biotechnology, vol. 5, 165-167 (1987).

Chrisey, Linda A et al., "Fabrication of Patterned DNA Surfaces", Nucleic Acids Research, vol. 24, No. 15, 3040-3047 (1996).

Wollenberger, Louis V. et al., "Detection of DNA Using Upconverting Phosphor Reporter Probes", SPIE, vol. 2985, 100-111 (1997).

Takara Bio, "Takara Bio to Produce DNA Fragments for DNA Microarrays on Industrial Scale", http://www.evaluategroup.com/Universal/View.aspx?type_Story&id.

Obeid, Pierre J. et al., "Microfabricated Device for DNA and RNA Amplification by Continuous-Flow Polymerase Chain Reaction and Reverse Transcription-Polymerase Chain Reaction with Cycle Number Section", Anal. Chem, 75, 288-295 (2003).

Supplemental European Search Report for Corresponding European Patent Application No. EP14820538.8, pp. 1-8 (dated Jan. 25, 2017).

Hashimoto, Masahiko et al., "Rapid PCR in a Continuous Flow Device", Lab Chip, 4, 638-645 (2004).

Thibaudau, Franck, "Ultrafast Photothermal Release of DNA from Gold Nanoparticles", J. Phys. Chem. Lett. 3, 902-907 (2012).

Berger, S.A. et al., "Flow in Curved Pipes", Ann. Rev. Fluid Mech., 15:461-512 (1983).

Written Opinion of the International Search Authority for PCT/US2015/013084 dated Apr. 17, 2015.

Ageno, M., et al., "The Alkaline Denaturation of DNA", Biophys J., Nov. 1969; 9(11): 1281-1311.

Hou, Sen, et al., "Method to Improve DNA Condensation Efficiency by Alkali Treatment", Taylor & Francis, Nucleosides, Nucleotides and Nucleic Acids, 28:725-735, 2009.

Thiel, Teresa, et al., "New zwitterionic butanesulfonic acids that extend the alkaline range of four families of good buffers: Evaluation for use in biological systems", J. Biochem. Biophys., Methods 37 (1998) 117-129.

Schulz, M.M., et al., "Archived or directly swabbed latent fingerprints as a DNA source for STR typing", Forensic Science International 127 (2002) 128-130.

Park, H., et al., "Stress response of fibroblasts adherent to the surface of plasma-treated poly(lactic-co-glycolic acid) nanofiber matrices", Colloids Surf B Biointerfaces, May 1, 2010 1;77(1); 90-5.

WiseGeek, "How Many Species of Bacteria Are There", http://www.wisegeek.org/how-many-species-of-bacteria-are-there.htm.

Wikipedia, "List of sequenced bacterial genomes", http://en.wikipedia.org/wiki/List_of_sequenced_bacterial_genomes.

Wikipedia, "Virus", http://en.wikipedia.org/wiki/Virus.

Agrawal, Sudhir, et al., "Site-Specific Functionalization of Oligodeoxynucleotides for Non-Radioactive Labelling", Tetrahedron Letters, vol. 31, No. 11, pp. 1543-1546, 1990.

Beija, Mariana, et al., "Synthesis and applications of Rhodamine derivatives as fluorescent probes", Chem. Soc. Rev., 2009, 38, 2410-2433.

Corstjens, P.L.A.M., et al., "Infrared up-converting phosphors for bioassays", IEE Proc.-Nanobiotechnol., vol. 152, No. 2, Apr. 2005.

Tyagi, Sanjay, et al., "Multicolor molecular beacons for allele discrimination", Nature Biotechnology, vol. 16, Jan. 1996.

Gibson, U.E., et al., "A novel method for real time quantitative RT-PCR", Genome Res., 1996, 6:995-1001.

Gupta, K.C., et al., "A general method for the synthesis of 3'-sulfhydryl and phosphate group containing oligonucleotides", Nucleic Acids Research, vol. 19, No. 11, p. 3019-3025 (1991).

Heid, C.A., et al., "Real time quantitative PCR", Genome Res. 1996 6:986-994.

Holland, Pamela, M., et al., "Detection of specific polymerase chain reaction product by utilizing the 5' → 3' exonuclease activity of

(56) References Cited

OTHER PUBLICATIONS

Thermus aquaticus DNA polymerase", Proc. Natl. Acad. Sci. USA, vol. 88, pp. 7276-7280, Aug. 1991, Biochemistry.

Hosokawa, Kazuo, et al., "DNA Detection on a Power-free Microchip with Laminar Flow-assisted Dendritic Amplification", Analytical Sciences, Oct. 2010, vol. 26.

Hussein, Ebtissam, H.A., et al., "Molecular Characterization of Cotton Genotypes Using PCR-based Markers", Journal of Applied Sciences Research, 3(10): 1156-1169, 2007.

Ibrahim, Rashid Ismael Hag, et al., "Complete Nucleotide Sequence of the Cotton (*Gossypium barbadense* L.) Chloroplast Genome with a Comparative Analysis of Sequences among 9 Dicot Plants", Genes Genet. Syst. (2006) 81, p. 311-321.

Jiang, Chun-Xiao, et al., "Polyploid formation created unique avenues for response to selection in *Gossypium* (cotton)", Proc. Natl. Acad. Sci. USA, vol. 95, pp. 4419-4424, Apr. 1998.

Kaneda, Shohei, et al., "Modification of the Glass Surface Property in PDMS-Glass Hybrid Microfluidic Devices", Analytical Sciences, Jan. 2012, vol. 28.

Karahan, H.A., et al., "Improvements of Surface Functionality of Cotton Fibers by Atmospheric Plasma Treatment", Fibers and Polymers 2008, vol. 9, No. 1, 21-26.

Lee, Seung-Bum, et al., "The complete chloroplast genome sequence of Gossypium hirsutum: organization and phylogenetic relationships to other angiosperms", BMC Genomics 2006, 7:61.

Lee, Linda G., et al., "Allelic discrimination by nick-translation PCR with fluorogenic probes", Nucleic Acids Research, 1993, vol. 21, No. 16, 3761-3766.

Tyagi, Sanjay, et al., "Molecular Beacons: Probes that Fluoresce upon Hybridization", Nature Biotechnology, vol. 18, Mar. 1996.

Sproat, Brian S. et al., "The synthesis of protected 5'-mercapto-2', 5'-dideoxyribonucleoside-3'-O-phosphoramidites; uses of 5'-mercapto-oligodeoxyribonucleotides", Nucleic Acids Research, vol. 15, No. 12, 1987.

Nazarenko, I.A., et al., "A closed tube format for amplification and detection of DNA based on energy transfer", Nucleic Acids Research, 1997, vol. 25, No. 12, 2516-2521.

Nelson, Paul S., et al., "Bifunctional oligonucleotide probes synthesized using a novel CPG support are able to detect single base pair mutations", Nucleic Acids Research, vol. 17, No. 18, 1989.

International Preliminary Report on Patentability issued in PCT/US2013/065161 dated Apr. 21, 2015.

Written Opinion of the International Searching Authority issued in PCT/US15/21165 dated Jul. 2, 2015.

Tuzlakoglu, K., et al., "A new route to produce starch-based fiber mesh scaffolds by wet spinning and subsequent surface modification as a way to improve cell attachment and proliferation", Journal of Biomedical Materials Research Part A, 2009, Wiley Periodicals, Inc, p. 369-377.

Zuckermann, Ronald, et al., "Efficient methods for attachment of thiol specific probes to the 3'-ends of synthetic oligodeoxyribonucleotides", Nucleic Acids Research, vol. 15, No. 13, 1987.

Yang, XF, et al., "Fluorimetric determination of hemoglobin using spiro form rhodamine B hydrazide in a micellar medium", Talanta Nov. 12, 2003; 61(4): 439-45.

Ullrich, Thomas, et al., "Competitive Reporter Monitored Amplification (CMA)—Quantification of Molecular Targets by Real Time Monitoring of Competitive Reporter Hybridization", Plos One, Apr. 2012, vol. 7, Issue 4.

Van De Rijke, Frans, et al., "Up-converting phosphor reporters for nucleic acid microarrays", Nature Publishing Group, Nature Biotechnology 19, Mar. 2001, 273-276.

Whitcombe, David, et al., "Detection of PCR products using self-probing amplicons and fluorescence", Nature Biotechnology, vol. 17, Aug. 1999, p. 804-807.

Hunicke-Smith, Scott P., "PCR and Cycle Sequencing Reactions: A New Device and Engineering Model", Dissertation, Stanford University, pp. i-xiv and 1-200, May 1997.

\* cited by examiner

METHOD OF MARKING CELLULOSIC PRODUCTS

CROSS-REFERENCE TO RELATED APPLICATION

This application claims priority from U.S. Patent Provisional Ser. No. 62/320,946, filed Apr. 11, 2016, which is incorporated herein by reference.

TECHNICAL FIELD

The invention pertains to a method for marking cellulosic products, including cellulosic fibers and cellulosic films, and more particularly to a method for marking such products with a nucleic acid marker to identify and validate the origin or authenticity of the products or items manufactured using such products.

BACKGROUND OF THE INVENTION

Manufacturers have an interest in protecting the integrity and purity of their products that are fabricated from quality components and may be subject to mixing or dilution with less expensive, lower quality materials. Such adulteration and even outright counterfeit substitution of process feedstocks and production materials, received from suppliers to be processed by the manufacturers, often escapes detection until after the products are manufactured.

Counterfeiting and blending of high-end products in particular, with cheaper material, has become a major liability problem for many companies. The International Chamber of Commerce (ICC) reported that in 2008, counterfeited goods resulted in a loss of $650 billion in revenues and 2.5 million jobs. The ICC projected that the loss in revenues would exceed $1.7 trillion in 2015, which is equivalent to 2% of the world economy. In addition to revenue losses, a variety of counterfeit products have been implicated in serious health and safety issues.

SUMMARY OF THE INVENTION

In one embodiment, the present invention provides a method of marking a cellulosic product for authentication: The method includes adding a detectable nucleic acid marker to a cellulosic medium during a step in a process for production of a cellulosic product; and thereby incorporating the nucleic acid marker into the cellulosic product to provide a detectably-marked cellulosic product. The preferred cellulosic product is lyocell.

In another embodiment, the present invention provides a method of authenticating a cellulosic product: The method includes: adding a detectable nucleic acid marker to a cellulosic medium during a step in a process for production of a cellulosic product; thereby incorporating the nucleic acid marker into the cellulosic product to provide a detectably-marked cellulosic product including the nucleic acid marker; introducing the detectably-marked cellulosic product into a stream of commerce; detecting the presence of the nucleic acid marker in the cellulosic medium of the detectably-marked cellulosic product; and thereby authenticating the cellulosic product.

The present invention further provides a detectably-marked cellulosic product for authentication, including a cellulosic medium that includes a detectable nucleic acid marker incorporated into the cellulosic medium and/or onto the surface of the cellulosic medium of the cellulosic product.

DETAILED DESCRIPTION

Figure 1:
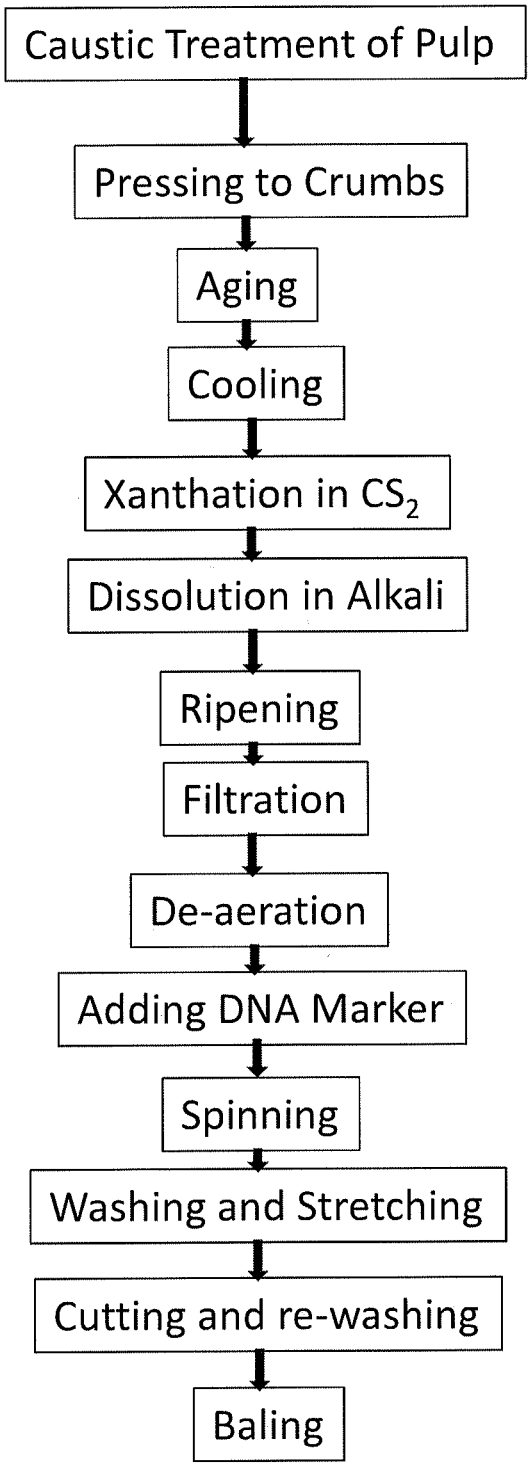
FIG. 1 shows a schematic of the steps of a process for the production of, a cellulosic fiber or film from cellulosic material.

Definitions of terms used herein:

"Cellulosic products" as used herein means cellulosic fibers such as for instance, viscose, lyocell or rayon; and cellulosic films, paper, cellulosic porous filters and cellulosic elastomeric sponges.

A "detectable nucleic acid marker" as used herein means any nucleic acid including at least in part, a unique sequence detectable by any of the many well known detection techniques, including polymerase chain reaction (PCR) techniques, other methods of DNA amplification such as isothermal, hybridization techniques and any of the well known method of DNA sequencing.

A "detectable marker DNA" as used herein means any DNA including at least in part, a unique sequence detectable by any of the many well known detection techniques, including polymerase chain reaction (PCR) techniques, other methods of DNA amplification such as isothermal, hybridization techniques and any of the well known method of DNA sequencing.

As used herein a "nucleic acid marker having a unique sequence" means a nucleic acid of one or more molecules having coherent nucleotide sequence shared by all the molecules.

As used herein "nucleic acid marker encoding information related to the product" means a nucleic acid marker having a nucleotide sequence designated to correlate with one or more segments of data related to the particular product. Such product-related information and the nucleotide sequence of the designated nucleic acid marker may be stored in a database. The database is useful for retrieving the product related information upon detection of the particular nucleotide sequence of the designated nucleic acid marker which thereby permits authentication or validation of the particular product from which the nucleic acid marker was obtained. The nucleic acid marker may be sampled at any stage during transit or in the stream of commerce to authenticate or validate the integrity of the product marked with the nucleic acid marker having the nucleotide sequence designated as related to the genuine product.

As used herein, "cellulosic material" includes plant matter (cotton, hemp, bamboo, and almost any botanical cellulosic material, as well as wood chips from beech, eucalyptus, and other trees). These cellulosic materials can be processed into a variety of different cellulosic products. Cellulosic materials are often mixed with solvents to manufacture cellulosic products.

A "cellulosic medium" may refer to any medium including cellulose, including but not limited to cellulosic dope.

The cellulosic medium may include cellulose from one or more cellulosic materials. The cellulosic medium may be a slurry or liquid bath in which cellulose pulp and additional chemicals are combined.

Viscose rayon is a semi-synthetic cellulosic material composed of cellulose and cellulose xanthate. It is a soft fiber commonly used in fabrics and clothing, linings, shirts, shorts, coats, jackets, and other outerwear. Viscose is also used in industrial yarns such as cords incorporated in tire manufacturing, upholstery and carpets, and for casting cellophane films.

Rayon fibers are formed of regenerated cellulose and can be engineered to meet many different needs due to the wide range of properties attainable by variation of the production processes. Examples include high wet-modulus rayon yarn, super absorbent rayons and highly stretched low water retaining rayon fibers.

Cellulosic products also include lyocell, another form of rayon, and reconstituted cotton based products. Lyocell is a cellulosic rayon product manufactured from bleached wood pulp and is used for making textiles for clothing and other purposes. Cellophane is a clear wrapping formed as a cellulosic film instead of being spun into fibers.

In a preferred embodiment, the invention relates to a method of incorporating detectable marker DNA into lyocell cellulosic fibers by incorporating detectable marker DNA into the lyocell's cellulosic medium during the pre-spinning stages of the fiber's manufacturing process.

Schematic Process Steps

See FIG. 1 for a schematic of steps in the manufacturing of cellulosic products, including treatment of cellulosic pulp with a caustic soda solution; pressing of the alkaline treated cellulosic material to fluffy crumbs; aging of the cellulosic material at controlled temperature for a set time; a cooling step; a "xanthation" processing step using carbon disulfide ($CS_2$) treatment and dissolution in lye and dissolving the yellow crumbs in caustic soda; a filtration step; a ripening step in which the cellulosic material is matured; a de-aeration step; a pre-spinning step (at which the detectable marker nucleic acid may be added); a washing step; a stretching step followed by a cutting and re-washing of the cellulosic product; and a drying and baling into bales of cellulosic product for distribution or shipping to downstream manufacturers.

Figure 2:
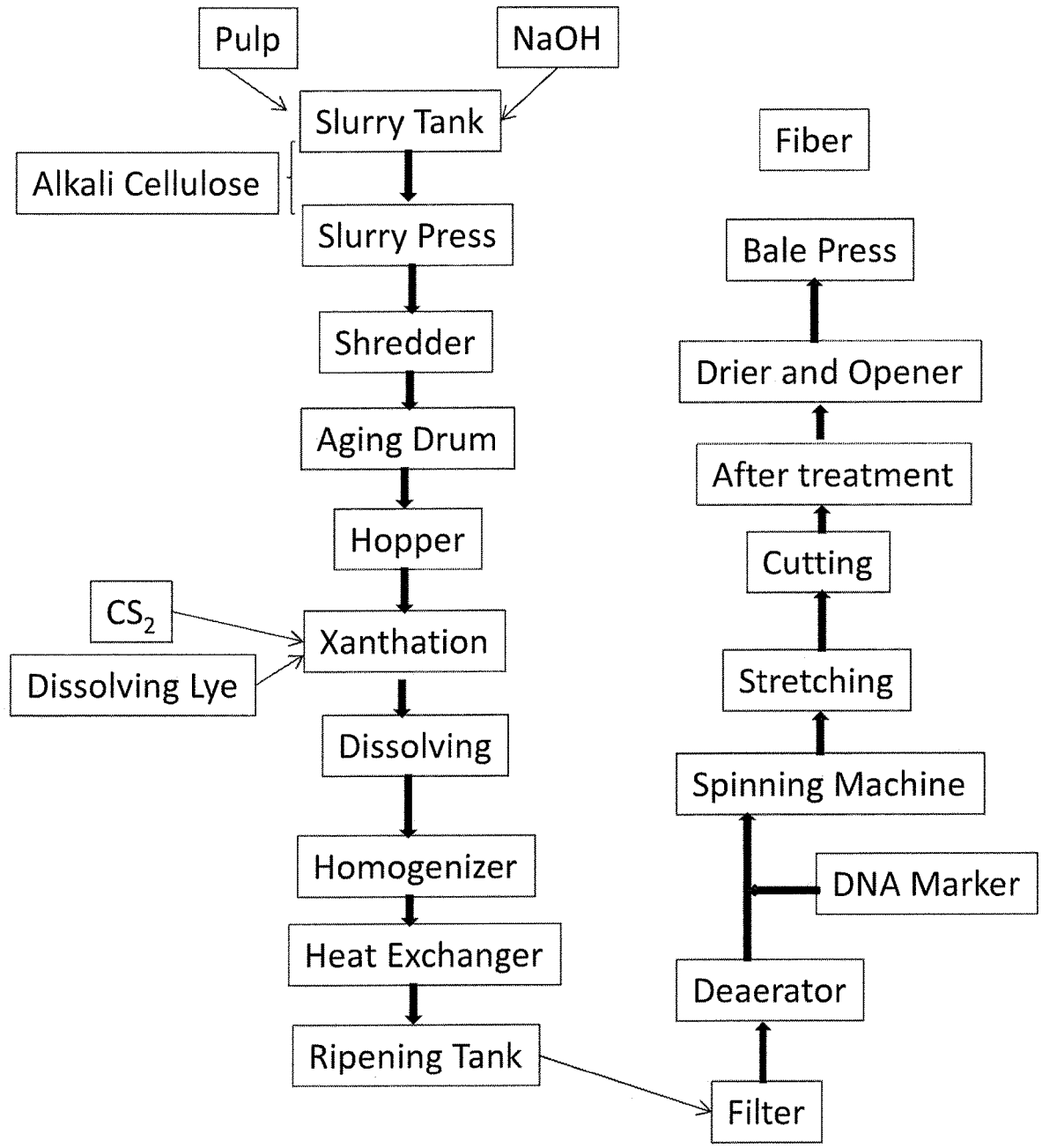
FIG. 2 shows a process for the production of a cellulosic fiber or film from wood chips, plant matter or other cellulosic material. One example of a step for addition of marker DNA is shown in the cellulosic medium immediately before spinning to produce the cellulosic fiber.

See FIG. 2 for a graphic representation of an exemplary process for the production of a cellulosic product showing addition of a DNA marker prior to spinning of fiber.

Figure 3:
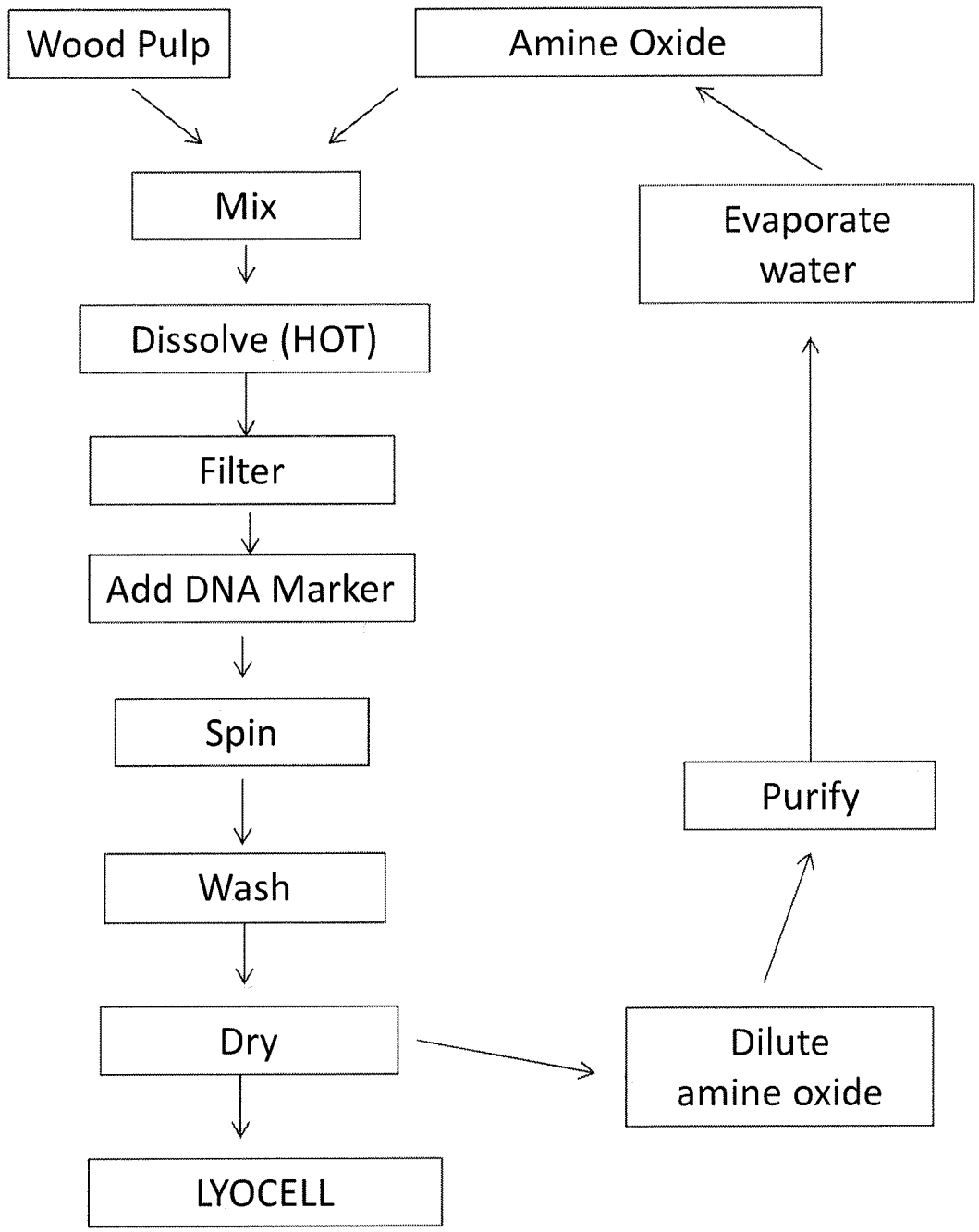
FIG. 3 shows the process of making lyocell, a cellulosic fiber.

See FIG. 3 for a schematic of steps in the manufacturing of lyocell. The process starts by mixing together wood pulp, water and amine oxide to create a cellulosic medium known as the cellulosic dope (The preferred amine oxide is N-methyl morpholine oxide (NMMO). The wood pulp dissolves into the solvent as a 1-1 mole complex of NMMO with water with heat and in a pressurized vessel. The solution is filtered. At this time, a detectable nucleic acid marker may be added to the cellulosic dope. Then, the cellulosic dope is pumped through spinnerets using the process of dry jet-wet spinning. After the spinning process, the fibers are washed with water and dried, then a lubricant may be applied to the fibers. The amine oxide solvent may be recovered from the fiber process and reused in the manufacturing process.

In an embodiment, the present invention provides a method of marking a cellulosic product for authentication: The method includes adding a detectable marker, such as for instance, and without limitation, a detectable nucleic acid to a cellulosic medium during a step in a process for production of a cellulosic product; and thereby incorporating and/or embedding the detectable marker into the cellulosic product to provide a detectably-marked cellulosic product. The step in the production of the cellulosic product may or may not be a step in which the cellulosic material is processed under alkaline conditions.

In one embodiment, the invention provides a method of marking a cellulosic product for authentication, including: adding a detectable nucleic acid marker to a cellulosic medium prior to or during the spinning or the filming of a cellulosic product, and thereby incorporating the detectable nucleic acid marker into the cellulosic product to provide a detectably-marked cellulosic product.

The detectably-marked cellulosic product produced by the above-listed methods may be any cellulosic fiber or cellulosic film.

Nucleic acids, especially deoxyribose nucleic acids (DNA) are well suited to use as detectable marker for ease of detection using modern methods such as isothermal amplification, polymerase chain reaction (PCR), and hybridization detection. Further, nucleic acids are ideally suited to encoding information due to the enormous coding capacity of DNA and RNA oligonucleotides. Useful information that can be readily encoded in nucleic acid detectable markers includes for instance and without limitation: the production lot number, the date of manufacture or processing, the time and the identity of the manufacturer.

Nucleic Acid Markers

Nucleic acids are particularly well suited to serve a detectable markers due to their enormous coding capacity and the fact that they can be used in such minute quantities that their sequences are impossible to duplicate without knowledge of their nucleotide sequences or access to a complementary probe or specific primer sequences necessary for their amplification and hence their detection.

The detectable nucleic acid marker is preferably attached directly onto or embedded directed into the cellulosic fibers or film. In the process of making lyocell, the nucleic acid marker should not be attached to any other "body" prior to being added to the cellulosic medium because adding a large "body" during the manufacturing process would degrade the internal structure of the end Lyocell fiber, which is typically less than 300 nm in width for lyocell. In fact, only trace (very small) amounts of detectable marker DNA are used in the process to ensure the uniform size and density of the internal fiber structure are not compromised.

Suitable amounts of detectable marker DNA for incorporation into the cellulosic material according to the present invention can range from 0.1 nanograms ($10^{-10}$ g) to micrograms ($10^{-6}$ g) of detectable marker DNA added per kilogram ($10^3$ g) of cellulosic material, with a preferred range of 0.1 nanogram ($10^{-10}$ g) to 10 micrograms ($10 \times 10^{-6}$ g) of detectable marker DNA added per kilogram of cellulosic material. The quantity of detectable marker DNA added during the processing of the cellulosic material may be carefully metered for optimal delivery of suitable amounts of DNA for authentication, validation and tracking, yet ensuring the structural integrity of the delicate resultant cellulosic products.

For example, the amount of detectable marker DNA added in the method of making lyocell may range from micrograms ($10^{-6}$ g) to less than a nanogram ($10^{-9}$ g) per kilogram of cellulosic material. In a preferred embodiment, the amount of detectable marker DNA added to the cellulosic medium in the method of making lyocell may range from 0.1 nanograms (10-10 g) to 10 micrograms ($10 \times 10^{-6}$ g) of detectable marker DNA added per kilogram of cellulosic material. In another embodiment, the amount of detectable marker DNA is less than 1 ppt ($10^{-12}$) w/w of the cellulosic material.

Suitable exemplary ranges of detectable marker DNA loading for cellulosic mediums include for instance:

A range from about 0.1 nanogram ($10^{-10}$ g) to about 10 microgram ($10 \times 10^{-6}$ g) of detectable marker DNA added per kilogram ($10^3$ g) of cellulosic material.

A range from about 0.1 nanogram ($10 \times 10^{-10}$ g) to about 1 microgram ($10^{-6}$ g) of detectable marker DNA added per kilogram ($10^3$ g) of cellulosic material.

A range from about 0.1 nanogram ($10 \times 10^{-10}$ g) to about 100 nanograms ($100 \times 10^{-9}$ g) of detectable marker DNA added per kilogram ($10^3$ g) of cellulosic material.

A range from about 0.1 nanogram ($10 \times 10^{-10}$ g) to about 10 nanograms ($10 \times 10^{-9}$ g) of detectable marker DNA added per kilogram ($10^3$ g) of cellulosic material.

A range from about 1 picograms ($1 \times 10^{-12}$ g) to about 100 microgram ($100 \times 10^{-6}$ g) of detectable marker DNA added per kilogram ($10^3$ g) of cellulosic material.

A range from about 1 femtogram ($10^{-15}$ g) to about 1 microgram ($10^{-6}$ g) of detectable marker DNA added per kilogram ($10^3$ g) of cellulosic material.

A range from about 10 femtograms ($10 \times 10^{-15}$ g) to about 100 nanograms ($100 \times 10^{-9}$ g) of detectable marker DNA added per kilogram ($10^3$ g) of cellulosic material.

A range from about 100 femtograms ($100 \times 10^{-15}$ g) to about 10 nanograms ($10 \times 10^{-9}$ g) of detectable marker DNA added per kilogram ($10^3$ g) of cellulosic material.

A range from about 1 picograms ($1 \times 10^{-12}$ g) to about 1 nanogram ($1 \times 10^{-9}$ g) of detectable marker DNA added per kilogram ($10^3$ g) of cellulosic material.

Any minimum value set forth herein may be combined with any maximum value set forth herein to create all possible ranges.

The detectable marker DNA having a unique nucleotide sequence may be included with an excess of a carrier nucleic acid of a natural genomic sequence or a mixture of random synthetic or natural nucleic acid sequences. In this way, extraction of total nucleic acid will not reveal the detectable marker DNA sequence without access to the cognate PCR primer pair or pairs for PCR, or the complementary nucleotide hybridization probe depending on the detection method used.

The detectable marker DNA used in the methods of the present invention may be any suitable DNA marker. The DNA may be single or double stranded DNA. In one embodiment, the detectable marker DNA may be from about 20 bases to about 5,000 kilobases in single strand length, or about 20 base pairs to about 5 Kb pairs in double strand length.

Alkaline Activation

The detectable marker DNA as used herein may be alkaline activated before introduction of the markers to the cellulosic materials via a cellulosic medium.

In one embodiment, the detectable marker DNA used in the methods of the present invention may be alkaline activated as described in US patent application publication US 20140256881 A1 "Alkaline Activation For Immobilization of DNA Taggants" of Berrada et al. the entire disclosure of which is hereby incorporated by reference.

In one embodiment, the alkaline conditions are produced by mixing the detectable marker DNA with an alkaline solution having a high pH, for instance the pH of the alkaline solution can be a pH of about 9.0 or higher; a pH of about 10.0 or higher; a pH of about 11.0 or higher, or even a pH of about 12.0 or higher, and contacting the deoxyribonucleic acid that has been exposed to the alkaline conditions with the cellulosic medium. In one embodiment, the alkaline solution is a solution of a hydroxide of an alkali metal.

In one embodiment, the method including exposing the detectable marker DNA to alkaline conditions, includes contacting the deoxyribonucleic acid that has been exposed to the alkaline conditions with the cellulosic medium; wherein the alkaline conditions are produced by mixing the detectable marker DNA with a solution of an alkali metal hydroxide, the alkali metal hydroxide solution having a concentration of from about 1 mM to about 1.0 M.

Alternatively, the alkali metal hydroxide solution may have a concentration of from about 10 mM to about 0.9 M. In another embodiment, the alkali metal hydroxide solution may have a concentration of from about 0.1 M to about 0.8 M. In still another embodiment, the alkali metal hydroxide solution may have a concentration of from about 0.4 M to about 0.8 M. In another embodiment, the alkali metal hydroxide solution may have a concentration of about 0.6 M.

In one embodiment, the detectable marker DNA is mixed with an alkaline solution having a pH from about 9.0 to about 14.0 and incubated at a temperature of from about 5° C. to about 55° C. to produce the alkaline conditions. Alternatively, the detectable marker DNA may be mixed with an alkaline solution having a pH from about 9.0 to about 14.0 and incubated at a temperature of from about 0° C. to about 65° C. to produce the alkaline conditions and incubating the mixture for a period of from about 1 minute to about 6 hours. In another embodiment, the alkaline treated detectable marker DNA may be added to the cellulosic medium immediately, for instance and without limitation, the alkaline treated detectable marker DNA may be added to the cellulosic medium in a cellulosic bath immediately prior to spinning the cellulosic medium into fibers or created cellulosic film.

In one embodiment, NaOH may be used for alkaline activation for incorporation of aqueous nucleic acids. As a potential consequence of the presence of NaOH in the some of the cellulosic process(es), nucleic acids may become alkaline activated via a side reaction. Thus, NaOH may be used to prevent "coagulation" of the dissolved cellulose by normalizing pH. In addition, other caustic solutions may be employed, such as potassium hydroxide, calcium oxide, alkoxides, and/or butyl-lithium.

Non-Activated DNA

The addition of NMMO (N-Methylmorpholine N-oxide) to cellulosic material will dissolve the cellulosic material to form a cellulosic medium (cellulosic dope). Following the dissolution process(es) of the cellulosic materials, the detectable marker DNA is incorporated into the cellulosic medium immediately preceding or during the re-polymerization/spinning step(s) for marking and authentication purposes. In this embodiment, the detectable marker DNA will not be alkaline activated.

In an exemplary embodiment, the detectable marker DNA is not alkaline activated, and is added to a cellulosic medium comprising wood pulp, NMMO and water, after dissolution of the cellulosic materials, but immediately preceding or during the re-polymerization/spinning step(s). In this instance, the detectable marker DNA may be delivered into the cellulosic medium as a saturated bound complex with a protecting agent, the protecting agent chosen from the following compounds: non aromatic alkyl amities such as tri-butyl amine, aromatic (triphenyl) alkyl amines such as crystal violet or methyl green, biological amines such as spermidine or spermine. The protecting agent acts to protect the detectable marker DNA from degradation caused by various aspects of the cellulosic medium, including but not limited to NMMO.

Metal ions, especially divalent metal ions are known to catalyze the hydrolytic degradation of nucleic acids. Therefore, addition of these metal ions in water and additives should be avoided where possible. Low concentrations of divalent metal ions commonly found in ground water can be removed by the addition of chelating agents.

The use of low concentrations of about 1 mM to about 20 mM of chelating agents such as Tris-EDTA for the sequestration of metal ions is well documented: See for instance "Metal Ion/Buffer Interactions" Fischer et al. (1979) Eur. J. Biochem. vol. 94: 523-530.

Alternatively, water softeners (e.g. amino acids such as glutamic acid and histidine, or organic dicarboxylic acids such as malate, and polypeptides such as phytochelatin, etc) may be used to sequester and or chelate metal ions, especially divalent metal ions.

Water quality can be a problem leading to lack of stability of the DNA detectable marker: this was found in many cases to be remedied by improving the water quality by removing divalent metal ions with a chelating agent.

Incorporation of Detectable Marker DNA

Surface coating of detectable marker DNA onto a cellulosic product exposes the detectable marker DNA to any further treatments and downstream processing which may lead to reduction in the amount of the detectable marker DNA surviving the processing, but this may be addressed by heavier initial loading of the detectable marker DNA onto the surface of the cellulosic product.

Incorporation of a detectable DNA marker by encapsulation within the cellulosic product rather than coating onto the surface of the cellulosic product protects the detectable DNA marker and preserve the ability to amplify the DNA by standard methods such as PCR and isothermal amplification for authentication. In another embodiment, the detectable DNA marker is integrated uniformly into the cellulosic fiber core and thus is protected from further downstream processing. Such encapsulation may require harsher conditions for extraction of the detectable DNA marker for adequate and reliable detection.

The detectable DNA marker may be added to the cellulosic material, via addition to the cellulosic medium, at any stage of the manufacturing of the cellulosic product. In one exemplary process, the detectable DNA marker may be added to the cellulosic material via addition to the cellulosic medium at the stage immediately before spinning/repolymerization into cellulosic fibers or extruding through a slit to form a cellulosic film. This procedure provides a cellulosic product which incorporates the detectable DNA marker throughout the cellulosic fiber or cellulosic film. The detectable DNA marker is present in the interior of the fiber or film as well as on the surface and so it is at least partially shielded from any further harsh treatments to which the cellulosic product may be exposed.

Alternatively, the detectable DNA marker may be applied to the surface of the cellulosic fibers or the cellulosic film. Higher loadings of the detectable DNA marker may be used to provide greater recoverability of the detectable DNA marker after surface treatments that may cause loss of some of the detectable DNA marker.

In another embodiment, the present invention provides a method of authenticating a cellulosic product including: adding a detectable marker such as for instance, and without limitation, a detectable nucleic acid encoding information related to the production process and/or the cellulosic product, to a cellulosic medium during a step in a process for production of a cellulosic product; thereby incorporating the detectable marker into the cellulosic product to provide a detectably-marked cellulosic product; introducing the detectably-marked cellulosic product into a stream of commerce; detecting the presence of the detectable marker in the cellulosic medium of the detectably-marked cellulosic product; and thereby authenticating the cellulosic product.

In another embodiment, the invention provides a method of authenticating a cellulosic product, including: adding a detectable nucleic acid marker to a cellulosic medium prior to or during the spinning or the filming of a cellulosic product; thereby incorporating the detectable nucleic acid marker into the cellulosic product to provide a detectably-marked cellulosic product; introducing the detectably-marked cellulosic product into a stream of commerce; detecting the presence of the detectable nucleic acid marker in the cellulosic medium of the detectably-marked cellulosic product; and thereby authenticating the cellulosic product. The cellulosic product may be any cellulosic product, such as for instance paper, or a cellulosic fiber, e.g. rayon, or a cellulosic film such as cellophane, a porous cellulosic filter, or an elastomeric cellulosic sponge.

The detectable nucleic acid marker may be a detectable DNA marker having a unique nucleotide sequence. In one embodiment, the unique nucleotide sequence of the detectable DNA marker may be used to encode information related to the process for production of the cellulosic product. The detectable DNA marker may or may not be alkaline activated prior to addition to the cellulosic medium during the cellulosic production process and may impart specific information about the cellulosic product, such as for instance, and without limitation, a production lot number, a date, a time and a manufacturer identity.

The present invention further provides a detectably marked a cellulosic product for authentication, including a cellulosic medium and a detectable marker, such as a nucleic acid marker incorporated into the cellulosic medium and/or onto the surface of the cellulosic product to form a detectably marked a cellulosic product.

In the event of a conflict between a definition recited in this specification and a definition provided in a patent or publication incorporated herein by reference, the definition provided herein is intended.

The disclosures of each of the references, patents and published patent applications disclosed herein are each hereby incorporated by reference herein in their entireties.

While the invention has been shown and described with reference to exemplary embodiments thereof, it will be understood by those of ordinary skill in the art that various changes in form and detail may be made therein without departing from the spirit and scope of the invention.

EXAMPLES

Example 1. DNA Tagging of Lyocell Dope (Cellulosic Material)

Wood pulp is mixed with defined mass excess solution of 50% NMMO, 50% water at room temperature to form a cellulosic medium. The cellulosic medium is then heated to solvate the cellulose and evaporate excess water to form the cellulosic medium.

DNA concentrate comprising detectable marker DNA is added to the cellulosic medium, at one of two (2) different times during the manufacturing process: The final mass ratio of detectable DNA marker to cellulosic material is typically between 0.1 nanograms to 10 micrograms per kilogram of cellulosic material. The addition point are:

A. Addition of detectable DNA marker at the beginning the heating period.

B. Addition of detectable DNA marker after the heating period, just before extrusion/spinning to form fiber.

Example 2. DNA Recovery from Lyocell Fibers

Four methods of DNA recovery and analysis from the lyocell may be used.

Method 1

Two-step in situ PCR of fiber, followed by standard CE (capillary electrophoresis):
  based on use of @10 mg (i.e 10 μL) of fiber per test. Fiber is added directly to a 40 uL PCR reaction Aqueous extraction of Fiber at 90° C. at pH 8 or greater, followed by charge switch magnetic bead concentration, then PCR/CE:
  based on the use of @100 mg (i.e 100 μL) of fiber per test.

Method 2

Aqueous extraction of fiber at 90° C. at pH 8 or greater, followed by charge switch magnetic bead concentration, followed by qPCR:
  based on use of @100 mg (i.e 100 μL) of fiber per test. An optimized DNA TaqMan assay may be deployed on a qPCR device Method 3

Solvation of fiber in 24% NaOH at 90° C. for 10 minutes, followed by neutralization with acetate and Nynal Magnetic Bead concentration, followed by qPCR:
  based on the use of @100 mg (i.e 100 μL) of fiber per test. An optimized DNA TaqMan assay may be deployed on a qPCR device Method 4

Solvation of fiber in 50% NMMO, 50% water at 90° C. followed by neutralization with acetate and Nynal Magnetic Bead concentration, followed by qPCR:
  based on the use of @100 mg (i.e 100 μL) of fiber per test. An optimized DNA TaqMan assay may be deployed on a qPCR device

The invention claimed is:

1. A method of authenticating a cellulosic product, comprising:
  adding a detectable nucleic acid marker to a cellulosic medium prior to or during a spinning step or prior to or during a filming step of processing of a cellulosic product, said cellulosic medium containing wood pulp and at least one chemical selected from the group consisting of carbon disulfide, sodium hydroxide or N-methylmorpholine-N-oxide (NMMO); and
  thereby incorporating the detectable nucleic acid marker into the cellulosic product to provide a nucleic acid-marked cellulosic product;
  introducing the nucleic acid-marked cellulosic product into a stream of commerce;
  detecting the presence of the detectable nucleic acid marker in the cellulosic product via dissolving all or a portion of the nucleic acid-marked cellulosic product into a solution and performing a PCR based detection technique on a sample of said solution; and
  thereby authenticating the cellulosic product.

2. The method according to claim 1, wherein the detectable nucleic acid marker comprises a detectable DNA marker.

3. The method according to claim 2, wherein the detectable DNA marker is added to the cellulosic medium in an amount ranging from 1 nanogram to 1 microgram of DNA per kilogram of cellulosic material.

4. The method according to claim 2, wherein the detectable DNA marker is added to the cellulosic medium in an amount ranging from 0.1 nanograms to 10 micrograms of DNA per kilogram of cellulosic material.

5. The method according to claim 2, wherein at least one of N-methylmorpholine-N-oxide (NMMO) or sodium hydroxide is used to dissolve all or a portion of the nucleic acid-marked cellulosic product into a solution.

6. The method according to claim 5, wherein information related to the process for production of the cellulosic product comprises one or more of a production lot number, a date, a time and a manufacturer.

7. The method according to claim 1, wherein the cellulosic product is a cellulosic fiber.

8. The method according to claim 7, wherein the cellulosic fiber is lyocell.

9. A method of marking a cellulosic product for authentication, comprising:
  adding a detectable DNA marker to a cellulosic medium prior to or during a spinning step or prior to or during a filming step of processing of a cellulosic product, said cellulosic medium containing wood pulp and at least one chemical selected from the group consisting of carbon disulfide, sodium hydroxide or N-methylmorpholine-N-oxide (NMMO), and wherein the DNA marker is complexed with at least one protecting agent chosen from the group consisting of non-aromatic alkyl amines, aromatic (triphenyl) alkyl amines, or biological amines; and
  thereby incorporating and embedding the detectable DNA marker throughout the cellulosic product to provide a DNA-marked cellulosic product.

10. The method according to claim 9, wherein the unique DNA sequence of the detectable DNA marker encodes information related to the process for production of the cellulosic product.

11. The method according to claim 10, wherein information related to the process for production of the cellulosic product comprises one or more of a production lot number, a date, a time and a manufacturer.

* * * * *